(12) United States Patent
Reichel et al.

(10) Patent No.: US 8,079,964 B2
(45) Date of Patent: Dec. 20, 2011

(54) METHOD AND APPARATUS FOR INSERTING BIOPSY SITE MARKER IN MARKER BODY

(75) Inventors: Lee E. Reichel, Springboro, OH (US); Gwendolyn P. Payne, Cincinnati, OH (US); Trevor W. V. Speeg, Williamsburg, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 969 days.

(21) Appl. No.: 12/036,506

(22) Filed: Feb. 25, 2008

(65) Prior Publication Data

US 2009/0216150 A1      Aug. 27, 2009

(51) Int. Cl.
  *A61B 5/103*  (2006.01)
  *A61B 5/117*  (2006.01)
(52) U.S. Cl. .............. 600/593; 600/1; 600/2; 600/3; 600/4; 600/562; 623/1.34; 424/1.25; 424/426
(58) Field of Classification Search .......... 600/562–572, 600/1–7; 606/167, 170, 180; 623/1.34; 424/1.25, 424/426
  See application file for complete search history.

(56) References Cited

U.S. PATENT DOCUMENTS

| | | | |
|---|---|---|---|
| 421,072 A | 2/1890 | Harris | |
| 2,828,744 A | 4/1958 | Hirsch et al. | |
| 4,787,384 A | 11/1988 | Campbell et al. | |
| 5,002,548 A | 3/1991 | Campbell et al. | |
| 5,024,727 A | 6/1991 | Campbell et al. | |
| 5,526,822 A | 6/1996 | Burbank et al. | |
| 5,853,366 A | 12/1998 | Dowlatshahi | |
| 5,906,574 A * | 5/1999 | Kan | 600/7 |
| 6,086,544 A | 7/2000 | Hibner et al. | |
| 6,161,034 A | 12/2000 | Burbank et al. | |
| 6,220,248 B1 | 4/2001 | Voegele et al. | |
| 6,228,055 B1 | 5/2001 | Foerster et al. | |
| 6,231,494 B1 * | 5/2001 | Verin et al. | 600/1 |
| 6,245,090 B1 * | 6/2001 | Gilson et al. | 606/213 |
| 6,270,464 B1 | 8/2001 | Fulton, III et al. | |

(Continued)

FOREIGN PATENT DOCUMENTS

WO    WO 97/17130    5/1997

OTHER PUBLICATIONS

U.S. Appl. No. 60/869,736, filed Dec. 13, 2006, Ritchie et al.

(Continued)

*Primary Examiner* — Max Hindenburg
*Assistant Examiner* — Rene Towa
(74) *Attorney, Agent, or Firm* — Frost Brown Todd LLC

(57) ABSTRACT

An apparatus for inserting a marking element into a marker body includes a body portion, an insertion member, and a pushing member. The body portion has a compartment configured to receive a marker body. The insertion member is configured to engage the marker body within the compartment. The pushing member is configured to engage with the insertion member. The pushing member is operable to force a marking element along the insertion member into the marker body. The insertion member may include a hollow needle configured to penetrate the marker body. The pushing member may include a pin configured to fit within the hollow needle. The marker body may include an opening such as a slit, a slot, or a passage that is configured to receive a marking element. The marker body may include a collagen dowel, and the marking element may be formed of titanium.

15 Claims, 14 Drawing Sheets

U.S. PATENT DOCUMENTS

| | | | |
|---|---|---|---|
| 6,270,472 B1 | 8/2001 | Antaki et al. | |
| 6,347,241 B2 | 2/2002 | Burbank et al. | |
| 6,356,782 B1 * | 3/2002 | Sirimanne et al. | 600/431 |
| 6,371,904 B1 | 4/2002 | Sirimanne et al. | |
| 6,427,081 B1 | 7/2002 | Burbank et al. | |
| 6,450,938 B1 | 9/2002 | Miller | |
| 6,544,185 B2 | 4/2003 | Montegrande | |
| 6,567,689 B2 | 5/2003 | Burbank et al. | |
| 6,626,849 B2 | 9/2003 | Huitema et al. | |
| 6,654,629 B2 * | 11/2003 | Montegrande | 600/424 |
| 6,662,041 B2 | 12/2003 | Burbank et al. | |
| 6,689,056 B1 * | 2/2004 | Kilcoyne et al. | 600/300 |
| 6,699,205 B2 | 3/2004 | Fulton, III et al. | |
| 6,725,083 B1 | 4/2004 | Burbank et al. | |
| 6,730,042 B2 | 5/2004 | Fulton et al. | |
| 6,824,507 B2 | 11/2004 | Miller | |
| 6,862,470 B2 | 3/2005 | Burbank et al. | |
| 6,889,833 B2 | 5/2005 | Seiler et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,063,681 B1 | 6/2006 | Peery | |
| 7,104,945 B2 | 9/2006 | Miller | |
| 7,229,417 B2 | 6/2007 | Foerster et al. | |
| 7,247,160 B2 | 7/2007 | Seiler et al. | |
| 7,329,414 B2 | 2/2008 | Fisher et al. | |
| 7,407,054 B2 | 8/2008 | Seiler et al. | |
| 7,429,240 B2 | 9/2008 | Miller | |
| 7,442,171 B2 | 10/2008 | Stephens et al. | |
| 7,465,279 B2 | 12/2008 | Beckman et al. | |
| 2003/0109803 A1 | 6/2003 | Huitema et al. | |
| 2004/0030262 A1 * | 2/2004 | Fisher et al. | 600/564 |
| 2004/0204660 A1 | 10/2004 | Fulton et al. | |
| 2004/0236213 A1 | 11/2004 | Jones et al. | |
| 2005/0033195 A1 | 2/2005 | Fulton et al. | |
| 2005/0080338 A1 | 4/2005 | Sirimanne et al. | |
| 2005/0085724 A1 | 4/2005 | Sirimanne et al. | |
| 2005/0119562 A1 | 6/2005 | Jones et al. | |
| 2005/0228311 A1 | 10/2005 | Beckman et al. | |
| 2006/0036159 A1 | 2/2006 | Sirimanne et al. | |
| 2006/0036165 A1 | 2/2006 | Burbank et al. | |
| 2006/0079770 A1 | 4/2006 | Sirimanne et al. | |
| 2006/0079805 A1 | 4/2006 | Miller et al. | |
| 2006/0079829 A1 | 4/2006 | Fulton et al. | |
| 2006/0084865 A1 | 4/2006 | Burbank et al. | |
| 2006/0122503 A1 | 6/2006 | Burbank et al. | |
| 2006/0155190 A1 | 7/2006 | Burbank et al. | |
| 2006/0276680 A1 | 12/2006 | Seiler et al. | |
| 2007/0010738 A1 | 1/2007 | Mark et al. | |
| 2007/0016017 A1 | 1/2007 | Mark et al. | |
| 2007/0021714 A1 | 1/2007 | Miller | |
| 2007/0118048 A1 | 5/2007 | Stephens et al. | |
| 2007/0135711 A1 | 6/2007 | Chernomorsky et al. | |
| 2007/0142725 A1 | 6/2007 | Hardin et al. | |
| 2007/0254005 A1 | 11/2007 | Pathak et al. | |
| 2008/0033280 A1 | 2/2008 | Lubock et al. | |
| 2008/0039819 A1 | 2/2008 | Jones et al. | |
| 2008/0058640 A1 | 3/2008 | Jones et al. | |
| 2008/0195066 A1 | 8/2008 | Speeg et al. | |
| 2009/0192408 A1 | 7/2009 | Mark | |

OTHER PUBLICATIONS

U.S. Appl. No. 60/874,792, filed Dec. 13, 2006, Hibner et al.
U.S. Appl. No. 11/942,791, filed Nov. 20, 2007, Speeg et al.
U.S. Appl. No. 11/942,785, filed Nov. 20, 2007, Hibner et al.
U.S. Appl. No. 11/942,791, filed Nov. 20, 2007, Johnson et al.
U.S. Appl. No. 60/869,736, filed Dec. 13, 2006, Ritchie.
U.S. Appl. No. 60/874,792, filed Dec. 13, 2006, Hibner et al.
Partial European Search Report dated Jun. 17, 2009 for Application No. 09250485.

* cited by examiner

METHOD AND APPARATUS FOR INSERTING BIOPSY SITE MARKER IN MARKER BODY

BACKGROUND

Biopsy samples have been obtained in a variety of ways in various medical procedures using a variety of devices. An exemplary biopsy device is the MAMMOTOME device from Ethicon Endo-Surgery, Inc. of Cincinnati, Ohio. Biopsy devices may be used under stereotactic guidance, ultrasound guidance, MRI guidance, or otherwise. Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 21, 2007. The disclosure of each of the above-cited U.S. Patents, U.S. Patent Application Publications, U.S. Provisional Patent Applications, and U.S. Non-Provisional Patent Application is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK, MICROMARK, and CORMARK devices from Ethicon Endo-Surgery, Inc. of Cincinnati, Ohio. Further exemplary devices and methods for marking a biopsy site are disclosed in U.S. Pub. No. 2005/0228311, entitled "Marker Device and Method of Deploying a Cavity Marker Using a Surgical Biopsy Device," published Oct. 13, 2005; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. Patents and U.S. Patent Application Publications is incorporated by reference herein.

While several systems and methods have been made and used for marking a site within a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
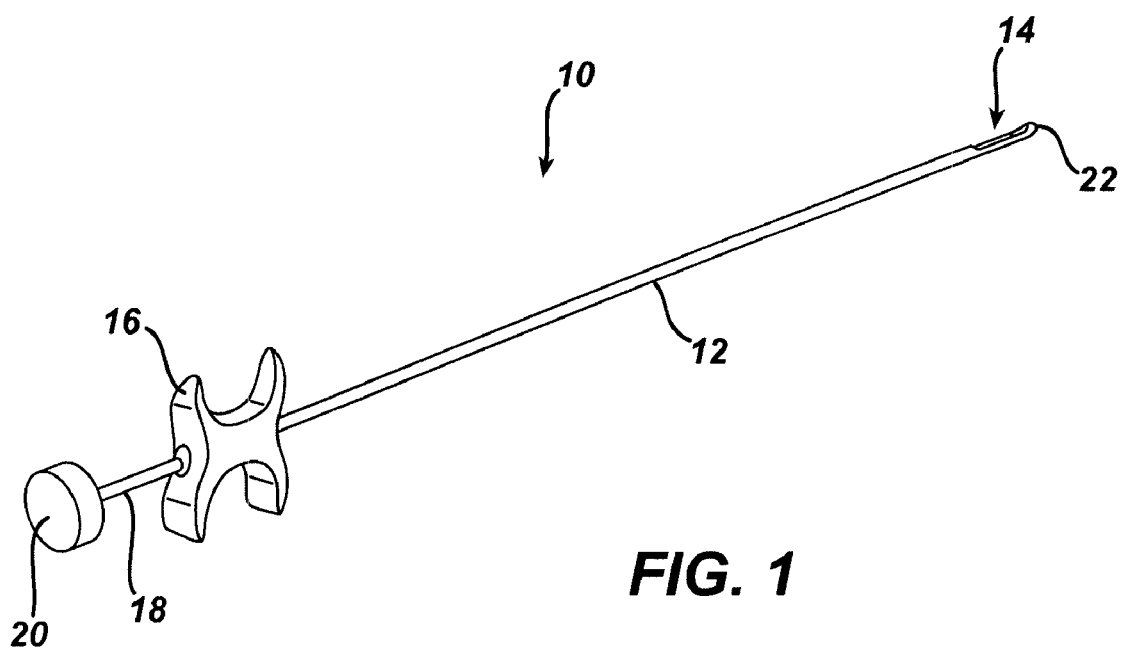
FIG. 1 depicts a perspective view of an exemplary marker deployment tool.

As shown in FIG. 1, an exemplary marker applier (10) includes an elongate outer cannula (12) having a transverse opening (14) formed near its distal end. The distal end of cannula (12) comprises a closed tip (22). A grip (16) is provided at the proximal end of cannula (12). Cannula (12) and tip (22) may be formed of PEBAX, any suitable polymer, metals, or any other suitable materials, including combinations thereof. A rod (18) is inserted in cannula (12) and is configured to translate within cannula (12). Rod (18) has sufficient rigidity to push a marker (30) out through opening (14) as will be described in greater detail below. However, rod (18) and cannula (12) are nevertheless flexible in this example. A plunger (20) is provided at the proximal end of rod (18) for forcing rod (18) distally in cannula (12). In particular, a user may grasp grip (16) with two fingers, and may push on plunger (20) using the thumb on the same hand, such that applier (10) may be operated by a user's single hand. A spring (not shown) or other feature may be provided about rod (18) to bias rod (18) proximally.

Marker applier (10) may be used to deploy a marker (30) via opening (14) within tissue, such as to mark a particular location within a patient. By way of example only, a marker (30) may mark the site of a biopsy. Of course, there may be a variety of other contexts for marking a location in a patient's body. In the present example, however, marker applier (10) is introduced to a biopsy site using the same instrument or biopsy device that was used to collect a tissue sample from the biopsy site. Several such biopsy devices are disclosed in the various patents and patent applications that have been referred to and incorporated by reference herein, though any other biopsy devices may be used.

Figure 2:
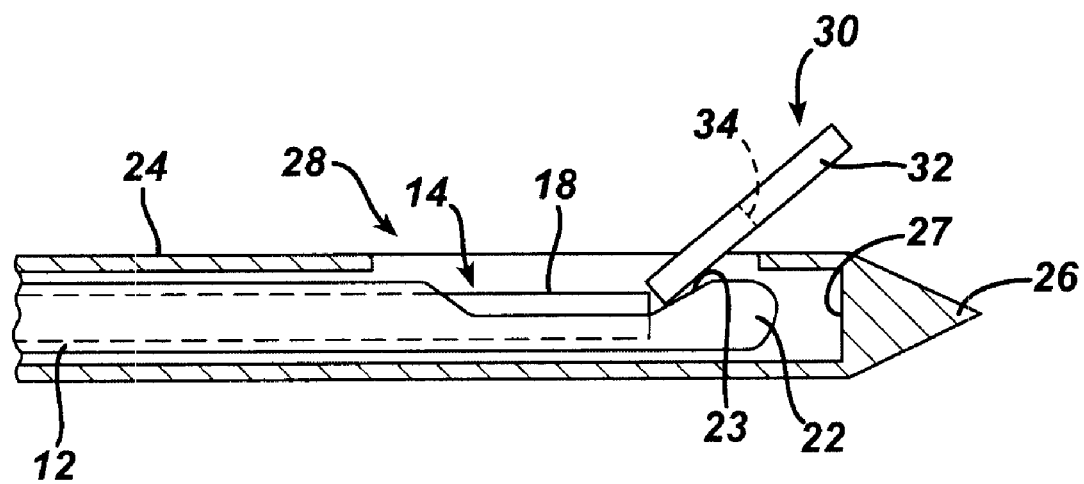
FIG. 2 depicts a partial cross-sectional view of the marker deployment tool of FIG. 1 inserted in an exemplary biopsy device, deploying a marker.

An exemplary use of a marker applier (10) is shown in FIG. 2. In particular, FIG. 2 shows the distal end of a marker applier (10) disposed within the outer needle (24) of a biopsy device. The outer needle (24) has a tissue piercing tip (26) and a transverse opening (28) proximal to the tip (26). In the present example, needle (24) and applier (10) are configured such that opening (14) of cannula (12) and opening (28) of needle (24) will be substantially aligned when cannula (12) is inserted in needle (24). In other words, opening (14) of cannula (12) is positioned relative to opening (28) of needle (24) such that a marker (30) may be deployed through both openings (14, 28). To deploy marker (30), a user actuates plunger (20), driving rod (18) distally. Tip (22) of marker applier (10) includes a proximally facing ramped surface (23), which urges marker (30) outwardly through openings (14, 28) and into the biopsy site as rod (18) is driven distally.

Marker (30) of the present example comprises a marker body (32) and a marking element (34). In some versions, marker body (32) is visible under ultrasound imaging, while marking element (34) is visible under MRI and X-ray, among other imaging modalities. For instance, marker body (32) may be formed of bovine collagen, cellulose, PLA/PGA, glycoprene, gelatinous materials such as hydrogel, and/or any other suitable material(s), including combinations thereof. Furthermore, marker body (32) may be biodegradable or bioapsorbable, or may have other properties. Marking element (34) may comprise a titanium wire, pellet, or other structure. Of course, any other material(s) may be used for marking element (34), including combinations thereof. In some versions, marker body (32) is formed of a square collagen pad that is folded and/or rolled about a titanium marking element (34) to form a substantially cylindraceous marker (30). Marker (30) is then compressed radially inward in this example before being inserted into cannula (12) to load marker applier (10) for deployment. Of course, marker (30) may have a variety of alternative configurations, may be formed using a variety of techniques, and may be used in a variety of other ways. Several merely illustrative examples of such variations will be described in greater detail below.

I. Marker Applier Distal End Variations

It will be appreciated in view of the teachings herein that a marker applier (10) may take a variety of forms and have a variety of configurations. Several such configurations will be described in greater detail below, while others will be apparent to those of ordinary skill in the art in view of the teachings herein.

Figure 3:
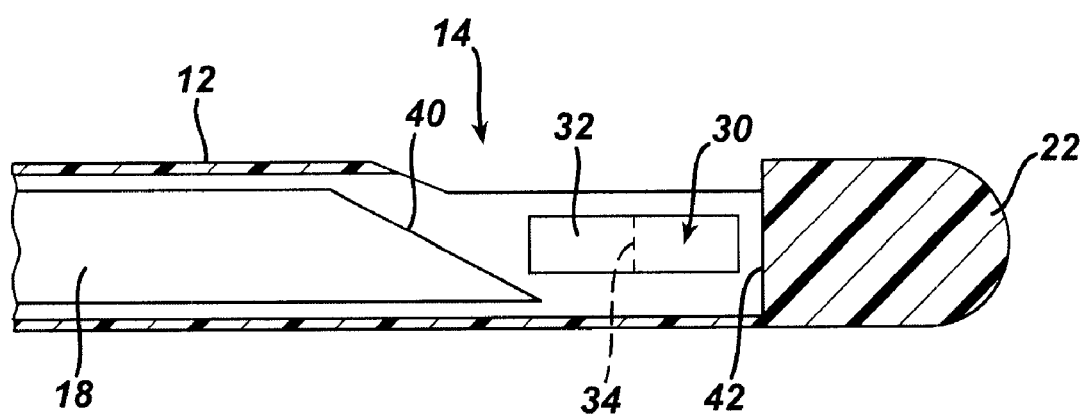
FIG. 3 depicts a partial cross-sectional view of an exemplary modification to the distal end of the marker deployment tool of FIG. 1.

As shown in FIG. 3, one merely exemplary modification to a marker applier (10) may include a distally facing ramped surface (40) on the distal end of rod (18). Suitable angles for ramped surface (40) will be apparent to those of ordinary skill in the art in view of the teachings herein. In the present example, tip (22) has a substantially flat proximally facing inner face (42). As rod (18) is driven distally by a user actuating plunger (20), ramped surface (40) engages marker (30). As marker (30) is engaged by both ramped surface (40) of rod (18) on one end and by flat inner face (42) of tip (22) on the other end, marker (30) is urged outwardly (e.g., radially outwardly) from cannula (12) via opening (14) into a site within a patient.

Figure 4:
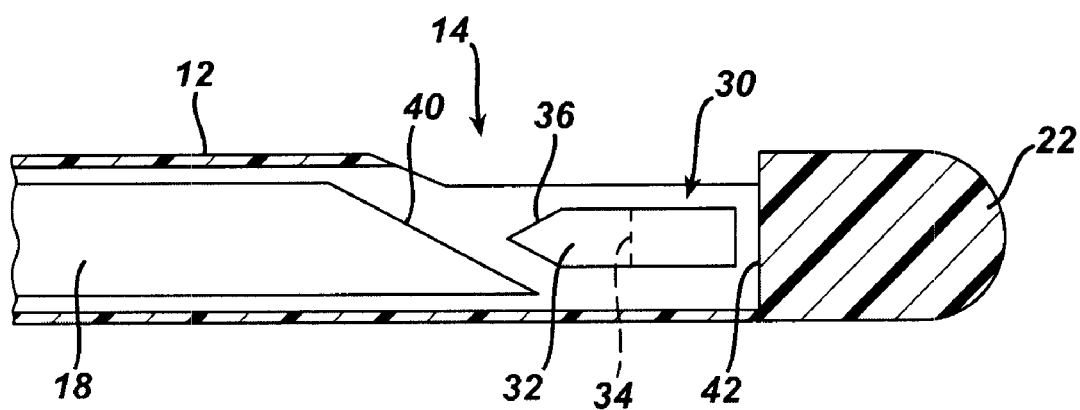
FIG. 4 depicts a partial cross-sectional view of another exemplary modification to the distal end of the marker deployment tool of FIG. 1.

A similar variation of marker applier (10) is shown in FIG. 4. In this example, marker applier (10) also includes a ramped surface (40) on the distal end of rod (18). In addition, tip (22) has a substantially flat inner face (42). However, marker (30) has an angled end (36) in this example. Suitable angles for angled end (36) will be apparent to those of ordinary skill in the art in view of the teachings herein. Angled end (36) may be formed in a variety of ways. For instance, angled end (36) may be substantially conical or frusto-conical. Alternatively, angled end (36) may be formed of two or more planar faces that converge at a common edge, face, or point. Other ways in which an angled end (36) of a marker (30) may be provided will be apparent to those of ordinary skill in the art in view of the teachings herein.

In the present example, angled end (36) is configured to interact with ramped surface (40) of rod (18). In particular, as rod (18) is driven distally by a user actuating plunger (20), ramped surface (40) engages angled end (36) of marker (30). As marker (30) is engaged by both ramped surface (40) of rod (18) on angled end (36) end and by flat inner face (42) of tip (22) on the other end, marker (30) is urged outwardly (e.g., radially outwardly) from cannula (12) via opening (14) into a site within a patient.

Figure 5:
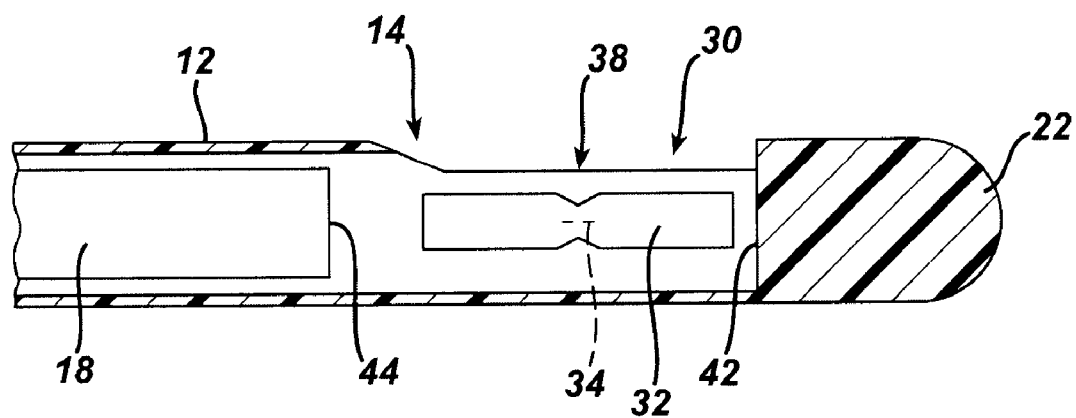
FIG. 5 depicts a partial cross-sectional view of another exemplary modification to the distal end of the marker deployment tool of FIG. 1.

Another variation of marker applier (10) is shown in FIG. 5. In this example, rod (18) has a substantially flat distal end (44) that is substantially parallel to the flat inner face (42) of tip (22). Alternatively, distal end (44) and/or inner face (42) may be ramped or have some other configuration. Marker (30) in this example has a recessed region (38) at its approximate center. Recessed region (38) may be formed about the entire circumference of marker (30). Alternatively, recessed region (38) may be formed of two or more substantially planar faces that converge at a common circumferential region. Other ways in which recessed region (38) may be configured will be apparent to those of ordinary skill in the art in view of the teachings herein. Recessed region (38) may be formed by cutting or otherwise removing material from marker body (32). Alternatively, recessed region (38) may be formed by compressing or crimping the center of marker body (32). Other ways in which recessed region (38) may be formed will be apparent to those of ordinary skill in the art in view of the teachings herein.

In the present example, marker (30) is configured such that, as rod (18) is driven distally, squeezing marker (30) between distal end (44) of rod (18) and inner face (42) of tip (22), marker body (32) bends or buckles at recessed region (38). Such bending may cause marker (30) to "pop out" of opening (14), thereby exiting cannula (12) into a biopsy site. In addition or in the alternative, such bending may cause marker body (32) to break in half and "pop out" of opening (14), thereby exiting cannula (12) into a biopsy site.

Figure 6:
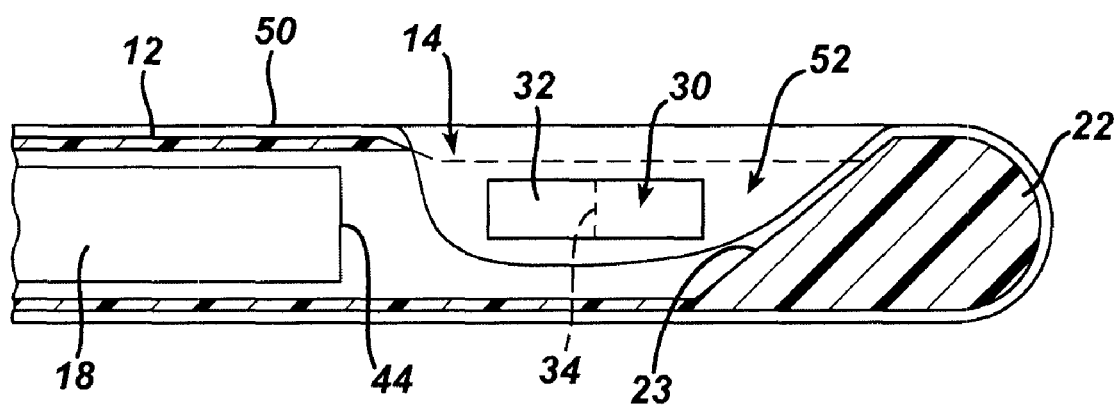
FIG. 6 depicts a partial cross-sectional view of another exemplary modification to the distal end of the marker deployment tool of FIG. 1.

Yet another variation of marker applier (10) is shown in FIG. 6. In this example, rod (18) has a substantially flat distal end (44), similar to the rod (18) shown in FIG. 5. Tip (22) has a ramped surface (23), similar to the tip (22) shown in FIG. 2. However, a thin plastic sheath (50) is provided about cannula (12) in this example. In particular, sheath (50) is disposed about the exterior of cannula (12), including tip (22). A portion of sheath (50) is recessed within opening (14) to provide a compartment (52), with marker (30) being carried external to sheath (50) within compartment (52). As rod (18) is driven distally, distal end (44) of rod (18) engages sheath (50), which urges marker (30) outwardly. In addition to or in lieu of distal movement of rod (18) to deploy marker (30), a portion of sheath (50) may be retracted proximally to urge marker (30) outwardly. For instance, a collar (not shown) or other component may be secured to sheath (50), such as near grip (16) of marker applier (10). Proximal retraction of sheath (50) (e.g., by pulling a collar proximally) may cause sheath (50) to become substantially taut. Such an increase in tightness of sheath (50) may draw compartment (52) outward, thereby urging marker (30) outward. Of course, sheath (50) may be provided and used in a variety of other ways, and may be incorporated with any of the other variations of marker applier (10) and markers (30) described herein.

Figure 7:
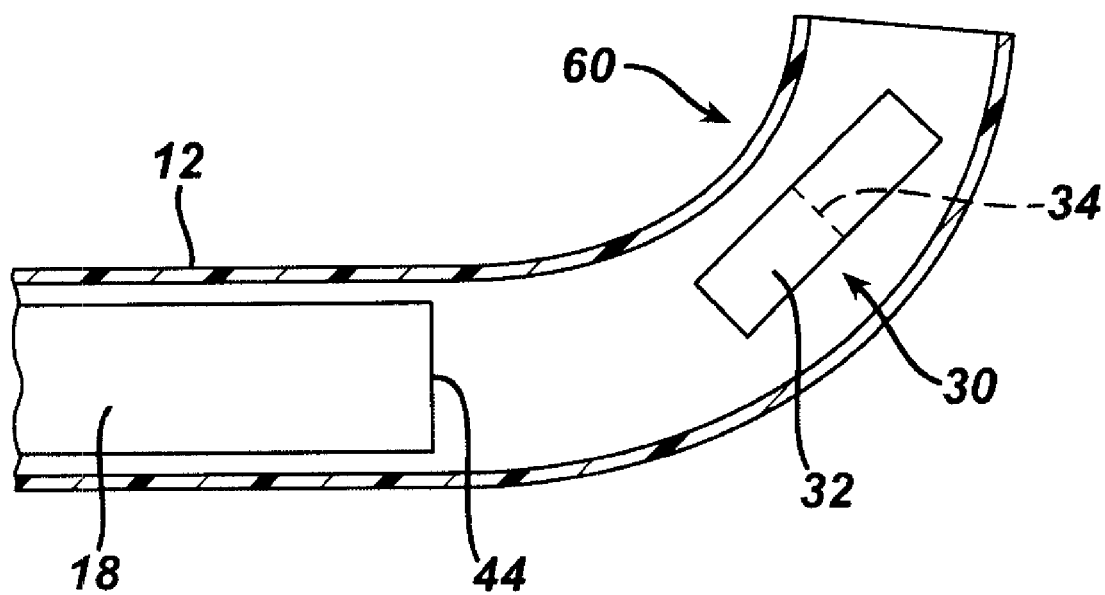
FIG. 7 depicts a partial cross-sectional view of another exemplary modification to the distal end of the marker deployment tool of FIG. 1.

Yet another variation of marker applier (10) is shown in FIG. 7. In this example, rod (18) has a substantially flat distal end (44), similar to the rod (18) shown in FIGS. 5-6. However, cannula (12) has an open and curved distal end (60) in this example. Distal end (60) of cannula (12) is configured such that, as rod (18) is driven distally, distal end (44) of rod (18) pushes marker (30) out through open distal end (60) of cannula (12) and into a biopsy site or other location within a patient. Rod (18) may have sufficient flexibility to substantially follow at least a portion of the curvature of distal end (60) of cannula (12) as rod (18) is driven distally within cannula (12). Alternatively, cannula (12), marker (30), and/or rod (18) may be configured such that rod (18) does not need to follow any portion of the curvature of distal end (60) in order to deploy marker (30).

In addition, distal end (60) of cannula (12) may be have sufficient resilience to allow cannula (12) to be advanced distally through a biopsy needle (24), such that distal end (60) is relatively straightened as cannula (12) is advanced within biopsy needle (24). When distal end (60) reaches opening (28) of biopsy needle (24), distal end (60) may then "pop" outward, due to the resiliency of the material forming distal end (60). Distal end (60) may thus re-form back to a curved configuration upon reaching opening (28) of biopsy needle (24). In some versions, cannula (12) is molded with distal end (60) in a curved configuration to provide such resilience. Other ways of configuring and forming distal end (60) will be apparent to those of ordinary skill in the art in view of the teachings herein. In addition, a suitable radius of curvature or other form of curvature for distal end (60) will be apparent to those of ordinary skill in the art in view of the teachings herein.

Figure 8:
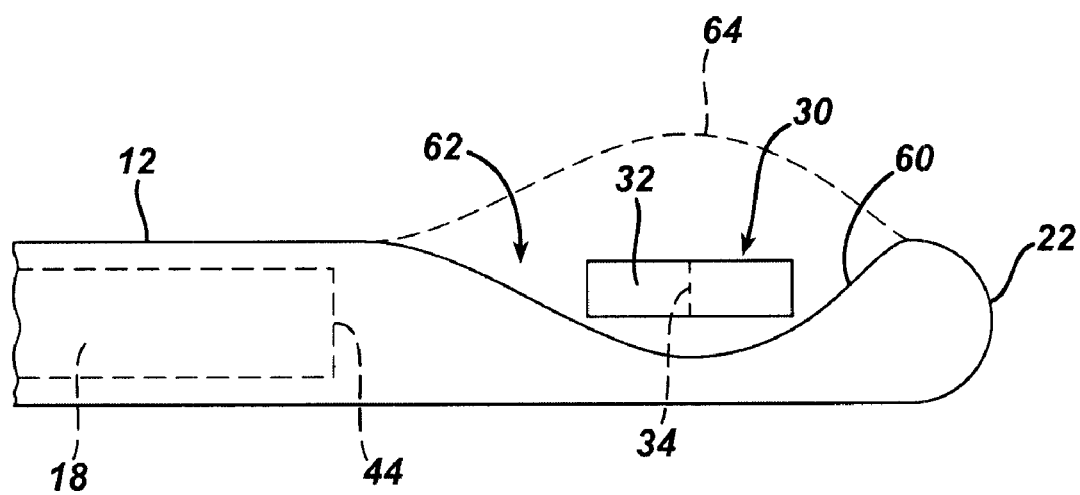
FIG. 8 depicts a partial view of another exemplary modification to the distal end of the marker deployment tool of FIG. 1.

Still another version of marker applier (10) is shown in FIG. 8. In this example, cannula (12) comprises a leaf spring (60) near tip (22). When bowed concavely inward, as shown in FIG. 8, leaf spring (60) forms a compartment (62) in which marker (30) is disposed. Leaf spring (60) may be formed by the same material that forms the remainder of cannula (12) (e.g., PEBAX, any suitable plastic, etc.), and/or may be unitarily formed with cannula (12). Alternatively, leaf spring (60) may be formed separately (e.g., formed of metal, some other plastic, etc.) and secured to cannula (12).

As shown in FIG. 8, leaf spring (60) is in a concave configuration, forming compartment (62), and storing potential energy. Upon sufficient actuation, however, leaf spring (60) "pops" outward to a convex configuration, thereby deploying marker (30) into a biopsy site or other location within a patient. An exemplary convex configuration of leaf spring (60) is shown by dashed line (64) in FIG. 8.

Leaf spring (60) may be actuated in a number of ways, such as by inducing buckling of leaf spring (60). For instance, rod (18) may be driven distally using plunger (20), thereby driving distal end (44) of rod (18) into leaf spring (60) to actuate leaf spring (60). Of course, rod (18) having a ramped surface (40) may also be used. Alternatively, the entire cannula (12) may be driven distally (e.g., by urging grip (16) distally), thereby driving tip (22) into the proximal face (27) of tip (36) of needle (24) of a biopsy device. Such driving of tip (22) into proximal face (27) may cause leaf spring (60) to buckle, thereby actuating leaf spring (60) into a convex configuration. An applier (10) may thus lack a rod (18), among other components, altogether. Still other ways in which leaf spring (60) may be actuated to deploy a marker (30) will be apparent to those of ordinary skill in the art in view of the teachings herein.

Any of the foregoing variations of a marker applier (10) may be engaged with a biopsy device in a variety of ways. In particular, a biopsy device may be configured to accept a marker applier (10) while at least a portion of the biopsy device is still inserted within a patient. In other words, a biopsy device may be used to acquire a tissue sample, and a marker applier (10) may be introduced through the biopsy device without having to withdraw or re-insert the biopsy device in tissue. For instance, a biopsy device may include an opening in the side of its housing, permitting a user to insert cannula (12) of marker applier (10) through the side opening and through the needle (24) of the biopsy device. A biopsy device may also include a passageway formed in a proximal portion of the biopsy device (e.g., a passageway coaxially aligned with needle (24)), permitting a user to insert cannula (12) of marker applier (10) through the proximal passageway and into the needle (24) of the biopsy device. A merely illustrative example of such a proximal passageway is disclosed in U.S. Non-Provisional application Ser. No. 11/942,791, entitled "Deployment Device Interface for Biopsy Device," filed Nov. 20, 2007, the disclosure of which is incorporated by reference herein. Still other ways in which a marker applier (10) may be used in conjunction with a biopsy device will be apparent to those of ordinary skill in the art in view of the teachings herein. Alternatively, a marker applier (10) may be used separately from a biopsy device, or in other procedures altogether.

II. Marker Body Variations

It will also be appreciated in view of the teachings herein that a marker (30) may take a variety of forms and have a variety of configurations. Several such configurations will be described in greater detail below, while others will be apparent to those of ordinary skill in the art in view of the teachings herein. In some versions of the examples shown in FIGS. 9-15 and described in greater detail below, the marker bodies are formed as collagen dowels, with marking elements inserted or otherwise disposed therein. However, it should be understood that a variety of other materials may be used to form the marker bodies. Furthermore, it should be understood that marking elements may be disposed on the outside of the marker bodies, in addition to or in lieu of marking elements being disposed within the marker bodies.

Figure 9A:
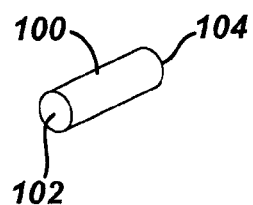
FIGS. 9A-9C depict perspective, plan, and end views of an exemplary marker.
Figure 9B:
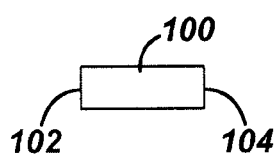
Figure 9C:
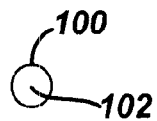

As shown in FIGS. 9A-9C, a marker body (100) comprises a dowel of bovine collagen. Marker body (100) has a substantially cylindraceous form, without cuts or slots being formed therein. A marking element (34) may be inserted within marker body (100) and/or located external to marker body (100) (e.g., wrapped around marker body (100), etc.). For instance, a marking element (34) may be inserted within marker body (100) using insertion device (200) described in greater detail below with reference to FIGS. 16-19 or using any other suitable devices or techniques. In some versions, after a marking element (34) has been inserted within marker body (100) and/or positioned about marker body (100), marker body (100) is compressed radially inward. Compression may also be applied to both ends (102, 104) of marker body (100). Marker body (100) is then positioned within cannula (12) of a marker applier (10), ready for deployment in a biopsy site or other location within a patient. Suitable lengths and diameters for marker body (100), as well as suitable methods of making a collagen dowel or other forms of marker body (100), will be apparent to those of ordinary skill in the art in view of the teachings herein.

Figure 10A:
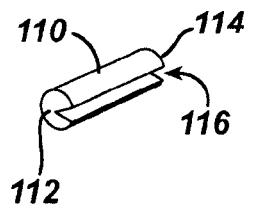
FIGS. 10A-10C depict perspective, plan, and end views of another exemplary marker.
Figure 10B:
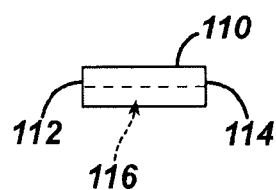
Figure 10C:
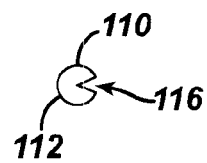

Another exemplary marker body (110) is shown in FIGS. 10A-10C. In this example, marker body (110) also comprises a collagen dowel, similar to marker body (100) described above, though other materials may be used as noted above. However, maker body (110) also has a longitudinal slit (116) formed therein. Slit (116) extends longitudinally from one end (112) of marker body (110) to another end (114) of marker body (110); and radially from the external surface of marker body (110) to the center of marker body (110). Slit (116) may be formed by cutting marker body (110), by crimping marker body (110), or using any other suitable technique. As best seen in FIG. 10C, slit (116) provides a profile of marker body (110) similar to a PAC-MAN character.

Slit (116) may be configured to facilitate incorporation of a marking element (34) into marker body (110). For instance, marker body (110) may be "opened" at slit (116), and a marking element (34) may then be inserted in slit (116), with marker body (110) then being "closed" at slit (116). Marker body (110) may then be compressed as noted above with respect to marker body (100). Alternatively, a marking element (34) may be inserted from an end (112, 114) of marker body (110) and/or may be inserted after marker body (110) is compressed. Other suitable ways in which one or more marking elements (34) may be incorporated with marker body (110) will be apparent to those of ordinary skill in the art in view of the teachings herein.

Figure 11A:
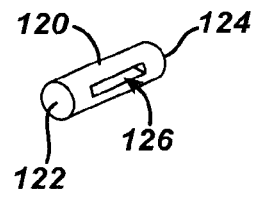
FIGS. 11A-11C depict perspective, plan, and end views of another exemplary marker.
Figure 11B:
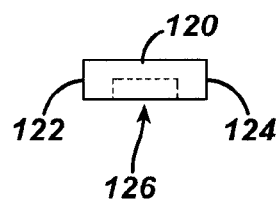
Figure 11C:
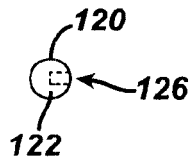

FIGS. 11A-11C show yet another merely exemplary marker body (120). In this example, marker body (120) also comprises a collagen dowel, similar to marker body (100) described above, though other materials may be used as noted above. A slot (126) is formed in marker body (120). The longitudinal boundaries of slot (126) are between ends (122, 124) of marker body (120), such that slot (126) does not extend along the full length of marker body (120). While slot (126) is shown as being approximately centered between ends (122, 124), opening (126) may have any other suitable longitudinal position. Slot (126) extends radially from the external surface of marker body (120) to the center of marker body (120). Alternatively, slot (126) may pass through marker body (120) entirely (e.g., extending along the full diameter of marker body (120)).

Slot (126) may be formed by cutting marker body (120), by punching marker body (120), or using any other suitable technique. Slot (126) in this example provides a region in which a marking element (34) may be inserted or otherwise positioned. In some versions, a piece (not shown) of marker body (120) is removed from marker body (120) to create slot (126), and that piece is replaced in slot (126) after marking element (34) is positioned in slot (126). In addition or in the alternative, marker body (120) may be compressed as described above before or after a marking element (34) is positioned in slot (126). Other suitable ways in which one or more marking elements (34) may be incorporated with marker body (120) will be apparent to those of ordinary skill in the art in view of the teachings herein.

Figure 12A:
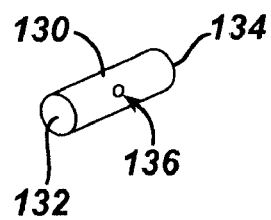
FIGS. 12A-12C depict perspective, plan, and end views of another exemplary marker.
Figure 12B:
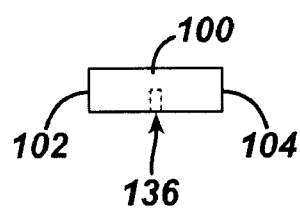
Figure 12C:
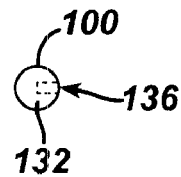

FIGS. 12A-12C show yet another merely exemplary marker body (130). In this example, marker body (130) also comprises a collagen dowel, similar to marker body (100) described above, though other materials may be used as noted above. Marker body (130) includes a transverse opening (136) formed therein. Transverse opening (136) is located between ends (132, 134) of marker body (130), and radially extends from the external surface of marker body (130) to the center of marker body (130). While opening (136) is shown as being approximately centered between ends (132, 134), opening (136) may have any other suitable longitudinal position.

Opening (136) may be formed by drilling marker body (130), by punching or poking marker body (130), or using any other suitable technique. Opening (136) in this example provides a region in which a marking element (34) may be inserted or otherwise positioned. A marking element (34) may be introduced to opening (136) transversely relative to marker body (130) or longitudinally relative to marker body (130). Marker body (130) may be compressed as described above before or after a marking element (34) is positioned in opening (136). Other suitable ways in which one or more marking elements (34) may be incorporated with marker body (130) will be apparent to those of ordinary skill in the art in view of the teachings herein.

Figure 13A:
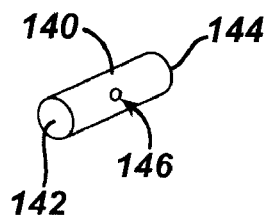
FIGS. 13A-13C depict perspective, plan, and end views of another exemplary marker.
Figure 13B:
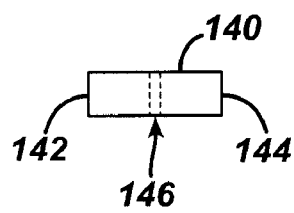
Figure 13C:
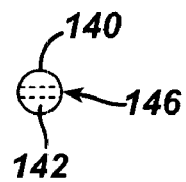

FIGS. 13A-13C show yet another merely exemplary marker body (140). In this example, marker body (140) also comprises a collagen dowel, similar to marker body (100) described above, though other materials may be used as noted above. In addition, marker body (140) has a transverse opening (146) positioned between ends (142, 144), similar to marker body (130) described above. However, unlike opening (136) of marker body (130), opening (146) of marker body (140) extends fully through marker body (140). Marker body (140) is otherwise substantially the same as marker body (130), and may incorporate a marking element (34) in the same ways as marker body (130) as noted above.

Figure 14A:
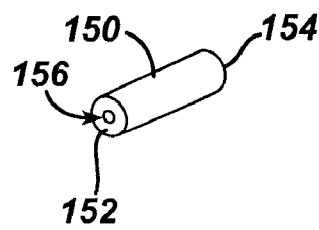
FIGS. 14A-14C depict perspective, plan, and end views of another exemplary marker.
Figure 14B:
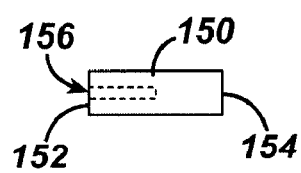
Figure 14C:
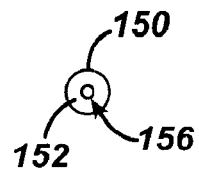

FIGS. 14A-14C show yet another merely exemplary marker body (150). In this example, marker body (150) also comprises a collagen dowel, similar to marker body (100) described above, though other materials may be used as noted above. Marker body (150) includes a longitudinal opening (156) formed therein. Longitudinal opening (156) extends from one end (152) of marker body (150) to the center of marker body (150), without reaching the other end (154) of marker body (150). While opening (156) is shown as being positioned along the axis defined by marker body (150), opening (156) may have any other suitable position.

Opening (156) may be formed by drilling marker body (150), by punching or poking marker body (150), or using any other suitable technique. Opening (156) in this example provides a region in which a marking element (34) may be inserted or otherwise positioned. A marking element (34) may be introduced to opening (156) transversely relative to marker body (150) or longitudinally relative to marker body (150). Marker body (150) may be compressed as described above before or after a marking element (34) is positioned in opening (156). Other suitable ways in which one or more marking elements (34) may be incorporated with marker body (150) will be apparent to those of ordinary skill in the art in view of the teachings herein.

Figure 15A:
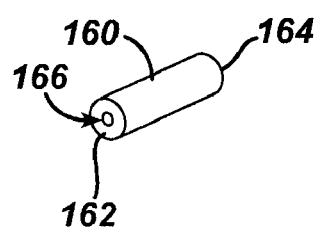
FIGS. 15A-15C depict perspective, plan, and end views of another exemplary marker.
Figure 15B:
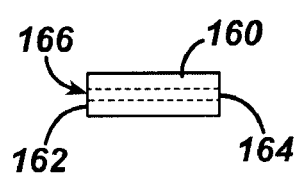
Figure 15C:
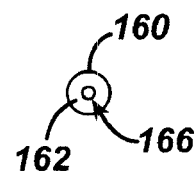
Figure 16:
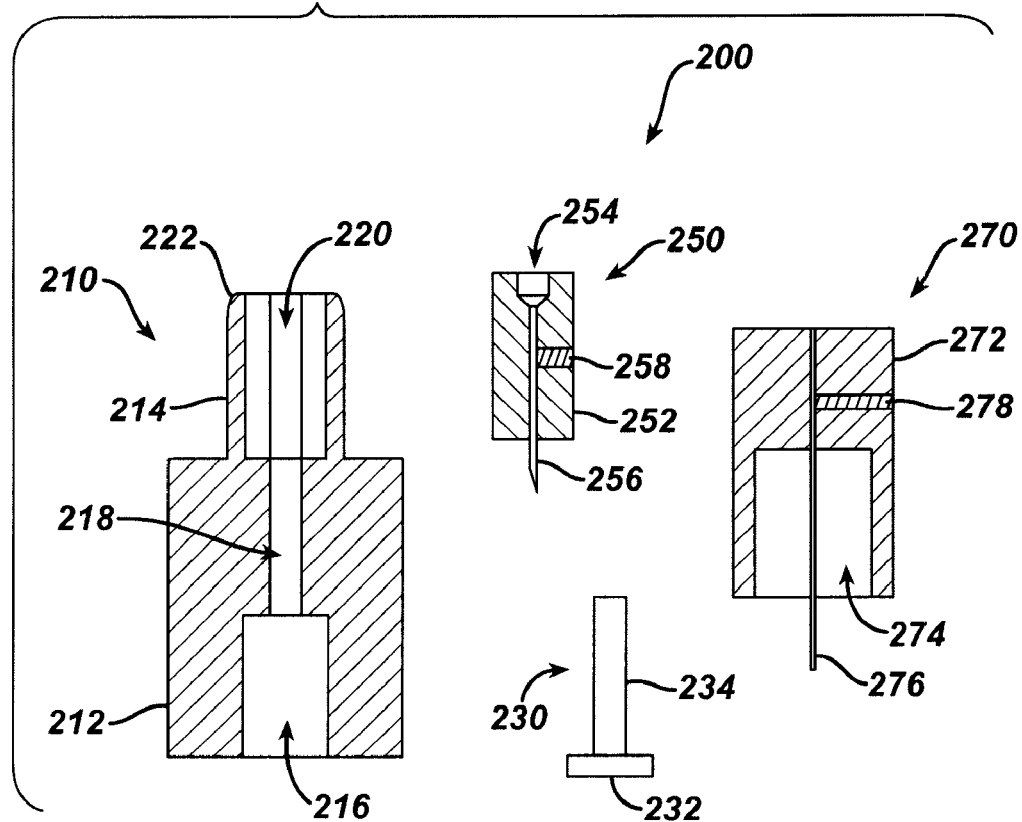
FIG. 16 depicts cross sectional views of components of an exemplary device for inserting a marker element into a marker body

FIGS. 15A-15C show yet another merely exemplary marker body (160). In this example, marker body (160) also comprises a collagen dowel, similar to marker body (100) described above, though other materials may be used as noted above. In addition, marker body (160) has a longitudinal opening (166) formed therein, similar to marker body (150) described above. However, unlike opening (156) of marker body (150), opening (166) of marker body (160) extends fully through the length of marker body (160) (i.e., from end (162) to end (164)). Marker body (160) is otherwise substantially the same as marker body (150), and may incorporate a marking element (34) in the same ways as marker body (150) as noted above.

The foregoing examples include a few of many different possible variations of a marker body (32). Still further variations of marker body (32) will be apparent to those of ordinary skill in the art in view of the teachings herein. In addition, while a single marker (30) is loaded in a marker applier (10) in the present example, it should be understood that a plurality of markers (30) may be loaded in a marker applier (10). For instance, each marker (30) in such a plurality may have characteristics that differ from other markers (30) in the plurality (e.g., different materials, different sizes, different shapes, different imageability, etc.). Alternatively, some or all of the markers (30) in such a plurality may have substantially the same if not identical characteristics. A plurality of markers (30) in a marker applier (10) may be deposited in the same biopsy site or other location within a patient, or they may be deposited in different locations within the patient.

III. Insertion of Marker into Marker Body

It will also be appreciated in view of the teachings herein that a variety of devices and techniques may be used to provide a marking element (34) within a marker body (30). A merely exemplary device (200) and technique will be described in greater detail below, while others will be apparent to those of ordinary skill in the art in view of the teachings herein.

As shown in FIGS. 16-19, a device (200) for inserting a marking element (34) in a marker body (32) includes a base member (210), a plug (230), a needle member (250), and a plunger (270). Base member (210) comprises a base portion (212) and a neck portion (214). A plug opening (216) is formed in the base portion (212). Plug opening (216) is configured to receive plug (230) as will be described in greater detail below. A marker opening (218) is also formed in base portion (212). Marker opening (218) is configured to receive a marker body (32) as will be described in greater detail below. Plug opening (216) has a greater diameter than marker opening (218) in this example, though in other versions, marker opening (218) may have the greater diameter, or openings (216, 218) may have substantially the same diameter. Neck portion (214) has a neck opening (220) formed therein, and has a chamfered edge (222). Of course, edge (222) need not necessarily be chamfered, and may be rounded, squared, or have any other suitable configuration. In addition, while openings (216, 218, 220) are all coaxially aligned in this example, openings (216, 218, 220) may have any other suitable relationships. For instance, marker opening (218) may be substantially perpendicular to neck opening (220).

Figure 17:
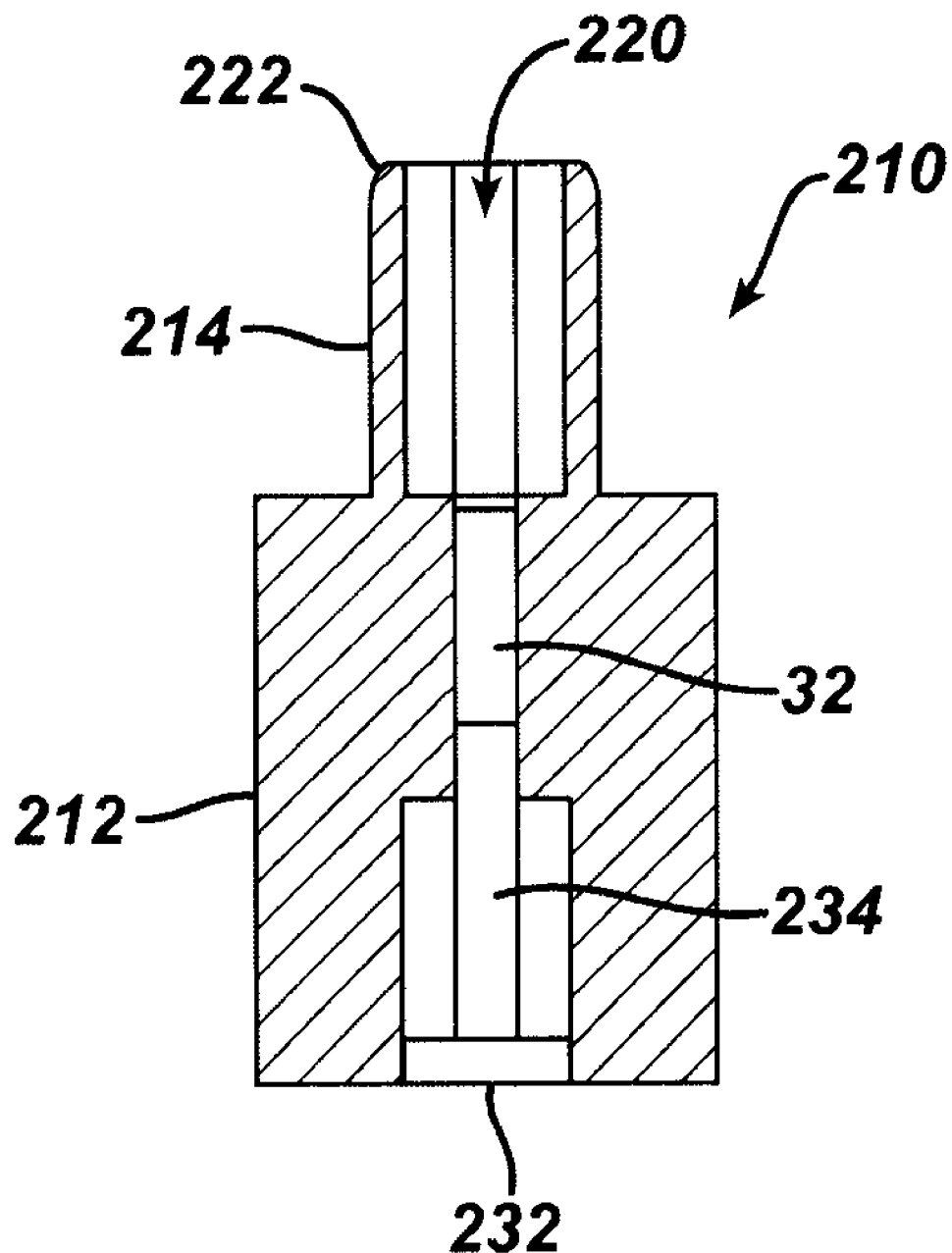
FIG. 17 depicts the device of FIG. 16 in an exemplary first stage of use.

Plug (230) of the present example comprises a generally circular head (232) and a stem (234). Head (232) has a diameter that is substantially equal to or less than the diameter of plug opening (216) in this example. Stem (234) has a diameter that is substantially equal to or less than the diameter of marker opening (218) in this example. In addition, plug (230) has a length that is greater than the length of plug opening (216). Accordingly, and as shown in FIG. 17, plug (230) may be inserted in plug opening (216), such that a portion of stem (234) extends into marker opening (218). This fit between plug (230) and base member (210) may be snug or loose, as desired. Alternatively, plug (230) and base member (210) may have any other suitable relationship.

Needle member (250) of the present example comprises a body (252), a top opening (254), and a hollow needle (256) that is positioned within and extends from body (252). Top opening (254) forms a funnel-like structure leading to the interior opening of hollow needle (256). A set screw (258) is positioned transverse to needle (256), and is operable to secure the longitudinal position of needle (256) relative to body (252). In other words, the longitudinal position of needle (256) relative to body (252) is adjustable in this example. Of course, set screw (258) may be eliminated, such that the longitudinal position of needle (256) relative to body (252) is substantially fixed, or any other suitable structures may be used.

Figure 18:
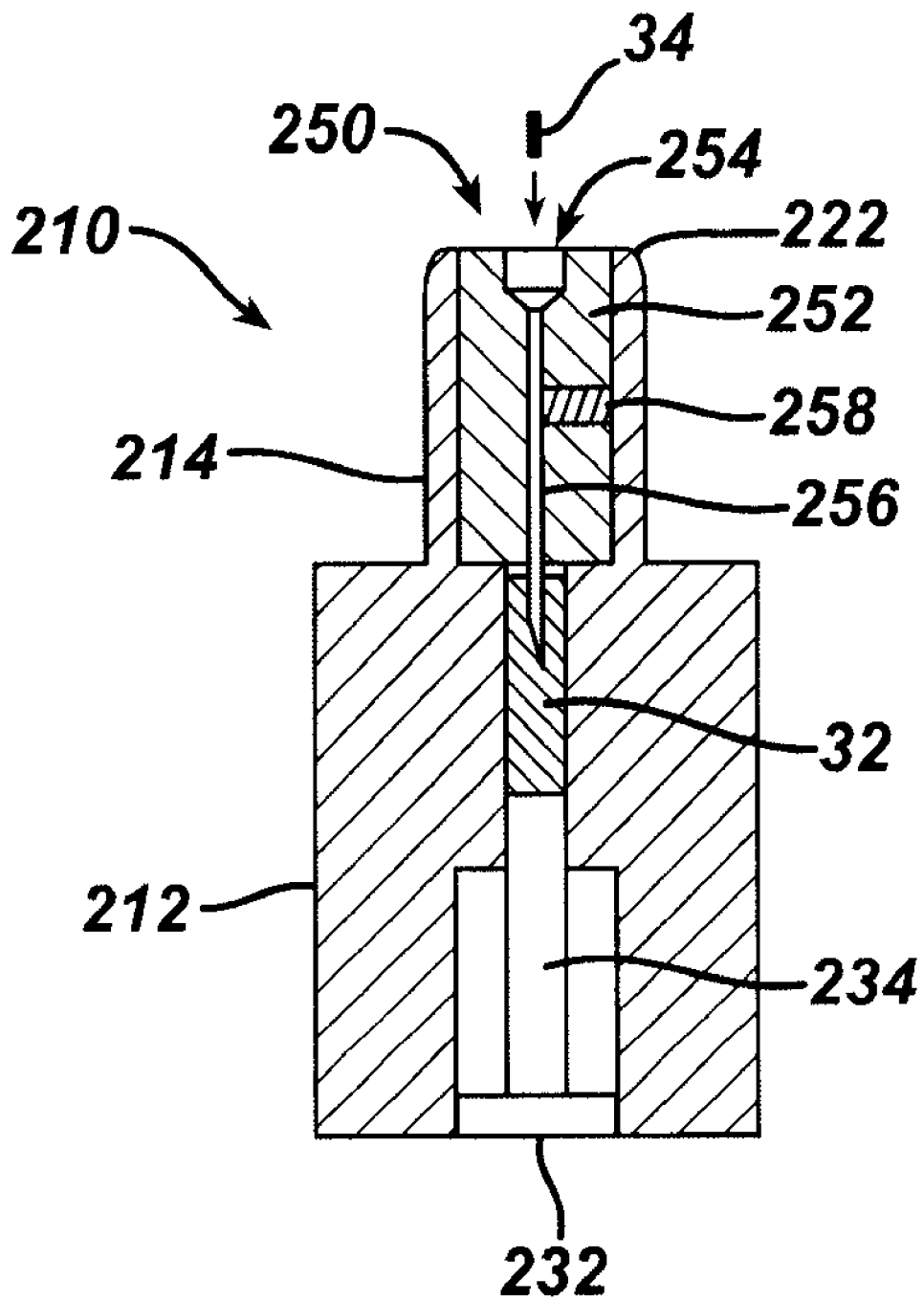
FIG. 18 depicts the device of FIG. 16 in an exemplary second stage of use.

Needle member (250) has a diameter that is substantially equal to or less than the diameter of neck opening (220) in this example. Needle member (250) may thus be inserted in neck opening (220). In addition, the lengths of neck opening (220), body (252), and needle (256) are such that needle (256) will extend into marker opening (218) when needle member (250) is inserted in neck opening (220), as shown in FIG. 18. The fit between needle member (250) and neck opening (220) may be snug or loose, as desired. Alternatively, needle member (250) and base member (210) may have any other suitable relationship.

Plunger (270) of the present example comprises a body (272), a hollow interior portion (274), and a pin (276). Pin (276) is centered within hollow interior portion (274), and extends from body (272). A set screw (278) is positioned transverse to pin (276), and is operable to secure the longitudinal position of pin (276) relative to body (272). In other words, the longitudinal position of pin (276) is adjustable in this example. Of course, set screw (278) may be eliminated, such that the longitudinal position of pin (276) relative to body (272) is substantially fixed, or any other suitable structures may be used.

Figure 19:
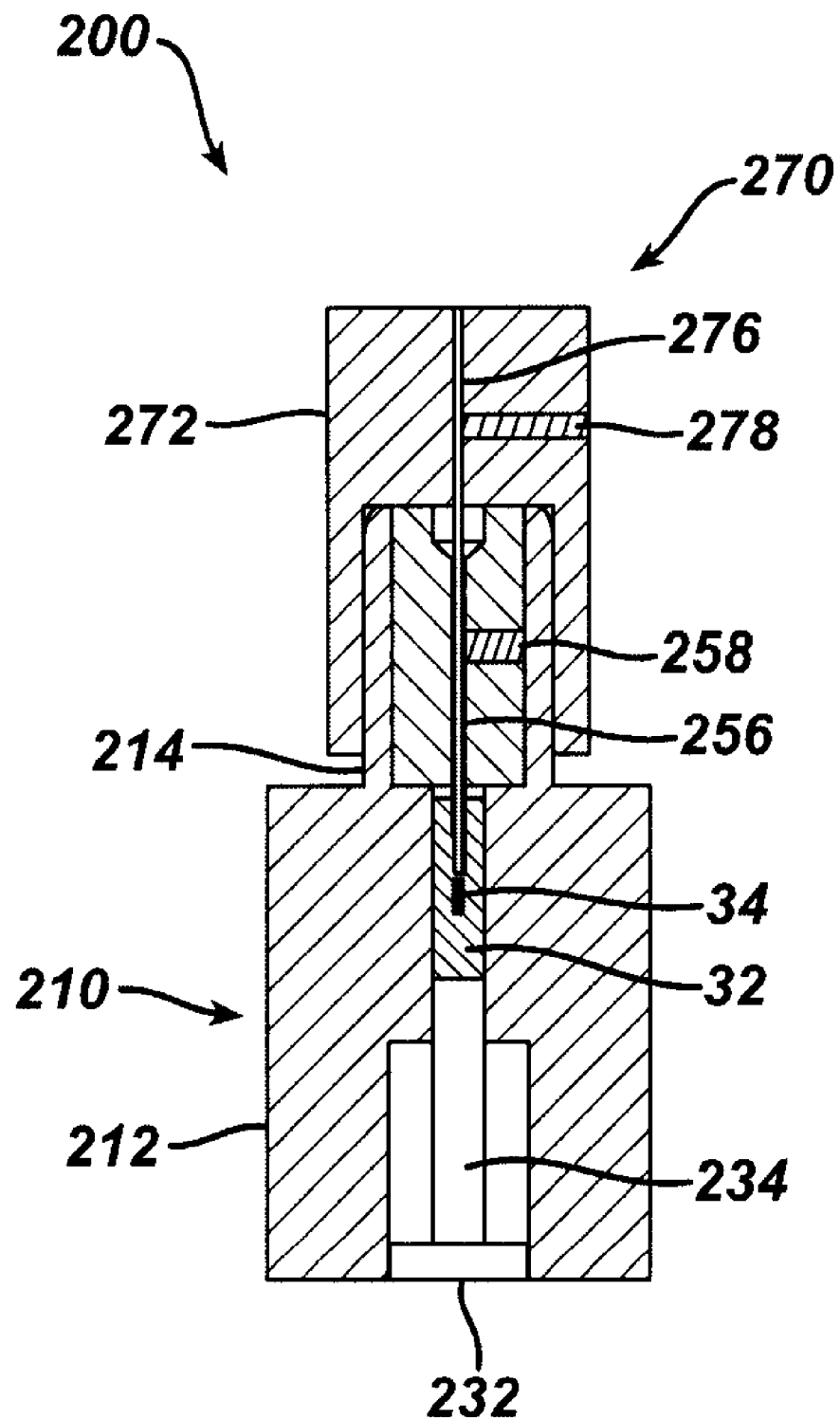
FIG. 19 depicts the device of FIG. 16 in an exemplary third stage of use.

Hollow interior portion (274) has a diameter that is substantially equal to or greater than the diameter of neck portion (214) in this example. Pin (276) has a diameter that is less than the inner diameter of hollow needle (256). Plunger (270) may thus be coupled with neck portion (256), such that hollow interior portion (274) receives neck portion (214). Chamfered edge (222) may facilitate such coupling. In addition, the lengths of neck portion (214), hollow interior portion (274), and pin (276) are such that pin (276) will extend through needle (256) when plunger (270) is coupled with neck portion (256), as shown in FIG. 19. In particular, pin (276) extends completely through needle (256) in this example. The fit between plunger (270) and neck portion (214) may be snug or loose, as desired. Alternatively, plunger (270) and base member (210) may have any other suitable relationship.

A series of steps in an exemplary use of marker insertion device (200) are illustrated in FIGS. 17-19. It should be noted that, while a marker body (32) is shown in each of FIGS. 17-19, marker body (32) is shown in cross-section in FIGS. 18-19 but not in FIG. 17. First, as shown in FIG. 17, plug (230) may be positioned in base member (210). After plug (230) has been positioned in base member (210), a marker body (32) is inserted into marker opening (218), as also shown in FIG. 17. This fit between marker body (32) and marker opening (218) may be snug or loose, as desired. Alternatively, marker body (32) and base member (210) may have any other suitable relationship.

Next, needle member (250) may be engaged with base member (210), as shown in FIG. 18. A marking element (34) may then be introduced through needle member (250). In particular, a marking element (34) may be dropped into top opening (254). The funnel-like configuration presented by top opening (254) in the present example may serve as a guide for marking element (34), leading toward the interior opening of hollow needle (256). The interior opening of hollow needle (256) may be sized such that it is slightly larger than marking element (34), permitting marking element (34) to pass through hollow needle (256). Prior to insertion of needle member (250) into neck opening (220), the longitudinal position of needle (256) may be adjusted such that the free tip of needle (256) will be located approximately at the center of a marker body (32) that is positioned in marker opening (218) when needle member (250) is inserted into neck opening (220). Alternatively, the tip of needle (256) may be longitudinally positioned just before or just past the center of marker body (32).

Then, after needle member (250) has been engaged with base member (210) as shown in FIG. 18 and a marking element (34) has been dropped into top opening (254), plunger (270) may be coupled with neck portion (214), as shown in FIG. 19. In particular, pin (276) may push marking element (34) completely through needle (256) and into marker body (32). Depending on the longitudinal position of needle (256) and pin (256), this may result in marking element (34) being positioned approximately at the center of marker body (32). Plunger (270) and needle member (250) may then be disengaged from base member (210), thereby withdrawing pin (276) and needle (256) from marker body (32), leaving marking element (34) within marker body (32).

Marker body (32) may then be removed from base member (210). For instance, head (232) of plug (230) may be pushed upward, such that stem (234) of plug (230) forces marker body (32) upward and into neck opening (220) where it can be easily extracted (e.g., pulled out, dumped out, etc.). Alternatively, plug (230) may be removed, and a poking instrument may be used to push marker body (32) upward and out through neck opening (220); or downward and out through plug opening (216). Other ways in which a marker body (32) may be removed from marker insertion device (200) will be apparent to those of ordinary skill in the art in view of the teachings herein.

It should be understood that marker insertion device (200), as well as methods of using marker insertion device (200), may be varied in numerous ways. By way of example only, plug (230) may be omitted. For instance, plug opening (216) may be replaced by an opening that has a smaller diameter than a marker body (32). Such an alternative opening may be small enough to restrict downward movement of marker body through base portion (212); yet be large enough to permit an instrument to be inserted therethrough to poke marker body (32) out through neck opening (220).

As another merely illustrative example of a variation for marker insertion device (200), marker opening (218) may be positioned transversely in base member (210). In other words, marker opening (218) may be oriented such that needle (256) and pin (276) may enter marker body (32) transversely rather than longitudinally. It will also be appreciated that marker insertion device (200) may be coupled with a pressing machine or other automated system, thereby automating the use of marker insertion device (200) to at least some degree. Still other ways in which marker insertion device (200) and its use may be varied will be apparent to those of ordinary skill in the art in view of the teachings herein.

Embodiments of the present invention may have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An apparatus for inserting a marking element into a marker body, the apparatus comprising:
   (a) a marker body having a first length, wherein the marker body comprises a bioresorbable portion;
   (b) a marking element wherein the marking element is insertable into the marker body, wherein the marking element has a second length, wherein the second length is less than the first length of the marker body;
   (c) a body portion having a compartment, wherein the marker body is disposed in the compartment;
   (d) an insertion member, wherein part of the insertion member is inserted in the marker body within the compartment; and (e) a pushing member, wherein the pushing member is configured to engage with the insertion member, wherein the pushing member is operable to force the marking element along the insertion member into the marker body;

wherein the marker body containing the marking element is insertable into a body cavity wherein the insertion member comprises a hollow needle; wherein the pushing member comprises a pin configured to pass through at least a portion of the hollow needle; wherein the pushing member further comprises a pushing body portion, wherein the pin extends from the pushing body portion; wherein the position of the pin relative to the pushing body portion is adjustable; wherein the pushing member further comprises a fixation member, wherein the fixation member is operable to selectively secure the position of the pin relative to the pushing body portion.

2. The apparatus of claim 1, wherein the needle has an open tip configured to penetrate the marker body.

3. The apparatus of claim 1, wherein the needle has a tip and a length selected to position the tip approximately at a center of the marker body.

4. The apparatus of claim 1, wherein the insertion member further comprises an insertion body portion, wherein the needle extends from the insertion body portion.

5. The apparatus of claim 4, wherein the position of the needle relative to the insertion body portion is adjustable.

6. The apparatus of claim 5, wherein the insertion member further comprises a set screw, wherein the set screw is operable to selectively secure the position of the needle relative to the insertion body portion.

7. The apparatus of claim 4, wherein the insertion body portion further comprises an opening in communication with the needle, wherein the opening has a ramped surface configured to guide the marking element into the needle.

8. The apparatus of claim 1, wherein the marker body defines an axis.

9. The apparatus of claim 8, wherein the insertion member comprises an elongate member configured to engage the marker body along the axis of the marker body.

10. The apparatus of claim 1, further comprising a plug member configured to engage the body portion, wherein the plug member is configured to restrict longitudinal motion of the marker body within the compartment.

11. The apparatus of claim 10, wherein the plug member is configured to engage a first end of the marker body.

12. The apparatus of claim 11, wherein the insertion member is configured to engage a second end of the marker body.

13. A method for inserting a marking element into a marker body, the method comprising:
(a) providing a marker insertion device having a body portion, wherein the body portion comprises a compartment configured to receive a marker body; wherein the marker insertion device comprises:
  (a) a marker body having a first length, wherein the marker body comprises a bioresorbable portion;
  (b) a marking element wherein the marking element is insertable into the marker body, wherein the marking element has a second length, wherein the second length is less than the first length of the marker body;
  (c) a body portion having a compartment, wherein the marker body is disposed in the compartment;
  (d) an insertion member wherein part of the insertion member is inserted in the marker body within the compartment; and
  (e) a pushing member, wherein the pushing member is configured to engage with the insertion member, wherein the pushing member is operable to force the marking element along the insertion member into the marker body; wherein the marker body containing the marking element is insertable into a body cavity; wherein the insertion member comprises a hollow needle; wherein the pushing member comprises a pin configured to pass through at least a portion of the hollow needle; wherein the pushing member further comprises a pushing body portion, wherein the pin extends from the pushing body portion; wherein the position of the pin relative to the pushing body portion is adjustable; wherein the pushing member further comprises a fixation member, wherein the fixation member is operable to selectively secure the position of the pin relative to the pushing body portion
(b) inserting a marker body in the compartment of the body portion, wherein the marker body comprises a bioresorbable portion;
(c) inserting a hollow needle into at least a portion of the marker body while the marker body is located within the compartment;
(d) introducing a marking element to the hollow needle;
(e) inserting a pin through the hollow needle to drive the marking element through the needle and into the marker body;
(f) extracting the hollow needle from the marker body while the marking element remains within the marker body; and
(g) extracting the marker body from the compartment.

14. The method of claim 13, wherein the marking element is radiopaque.

15. The method of claim 13, comprising inserting the marker body containing the marking element into a marker deployment tool.

* * * * *